US008040247B2

(12) United States Patent
Gunaratne

(10) Patent No.: US 8,040,247 B2
(45) Date of Patent: Oct. 18, 2011

(54) SYSTEM FOR RAPID DETECTION OF DROWSINESS IN A MACHINE OPERATOR

(75) Inventor: Pujitha Gunaratne, Windsor (CA)

(73) Assignee: Toyota Motor Engineering & Manufacturing North America, Inc., Erlanger, KY (US)

( * ) Notice: Subject to any disclaimer, the term of this patent is extended or adjusted under 35 U.S.C. 154(b) by 382 days.

(21) Appl. No.: 12/409,140

(22) Filed: Mar. 23, 2009

(65) Prior Publication Data

US 2010/0238034 A1    Sep. 23, 2010

(51) Int. Cl.
  *G08B 23/00*  (2006.01)
(52) U.S. Cl. .............. 340/575; 340/539.1; 340/5.83
(58) Field of Classification Search .............. 340/575, 340/573.1, 576, 539.1, 426.19, 989, 991, 340/539.11, 5.1, 5.81–5.83, 4.1
See application file for complete search history.

(56) References Cited

U.S. PATENT DOCUMENTS

| 5,689,241 | A | * | 11/1997 | Clarke et al. | 340/575 |
| 6,724,920 | B1 | | 4/2004 | Berenz et al. | |
| 7,027,621 | B1 | * | 4/2006 | Prokoski | 382/118 |
| 7,043,056 | B2 | * | 5/2006 | Edwards et al. | 382/103 |
| 7,336,804 | B2 | * | 2/2008 | Steffin | 382/104 |
| 7,482,937 | B2 | * | 1/2009 | Chai et al. | 340/576 |
| 2007/0159344 | A1 | * | 7/2007 | Kisacanin | 340/576 |
| 2008/0212828 | A1 | * | 9/2008 | Ishida et al. | 382/100 |
| 2009/0034796 | A1 | * | 2/2009 | Johns | 382/103 |

* cited by examiner

*Primary Examiner* — Daniel Previl
(74) *Attorney, Agent, or Firm* — Gifford, Krass, Sprinkle, Anderson & Citkowski, P.C.

(57) ABSTRACT

The present invention discloses a system and a process for rapidly detecting drowsiness in a individual operating a machine. The system can capture a plurality of facial images of the individual and compare one or more facial parameters from the images to a plurality of stored high priority sleepiness facial actions that are in a prioritized action database. Based on the comparison, a current level of sleepiness can be determined for the individual and an actuator can be actuated in order to alert the individual and possibly any other individuals that may be in the vicinity.

16 Claims, 5 Drawing Sheets

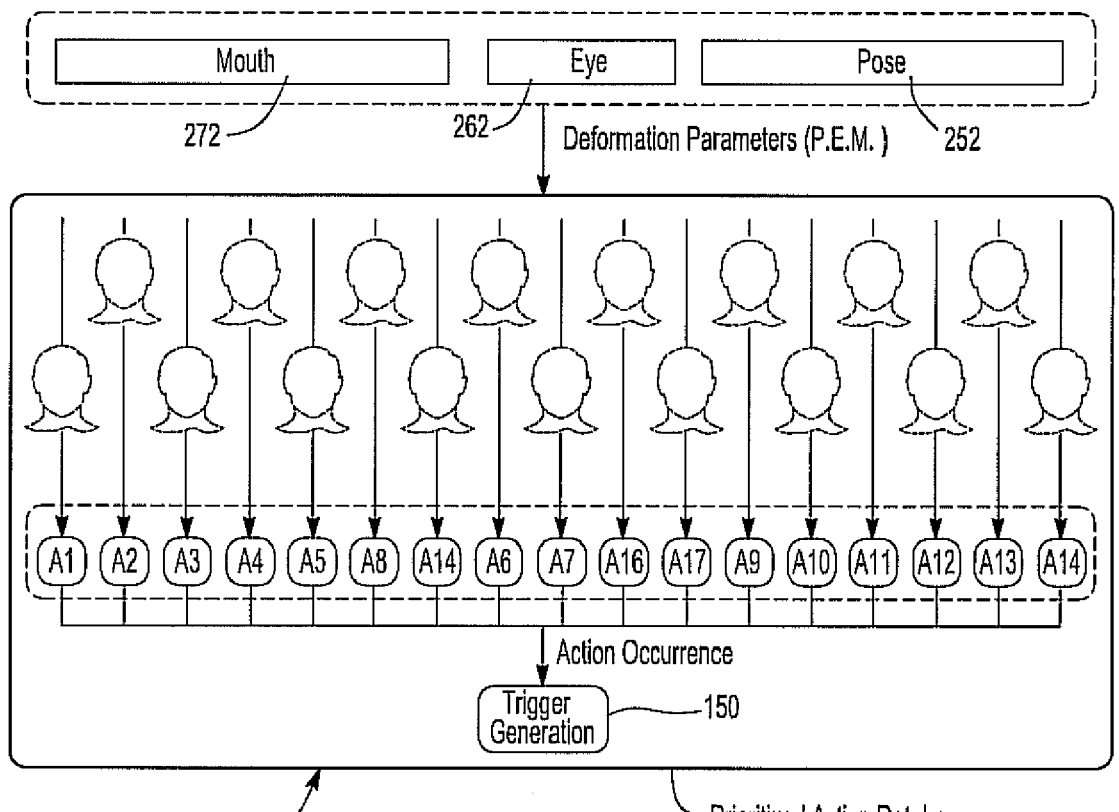
Fig-6
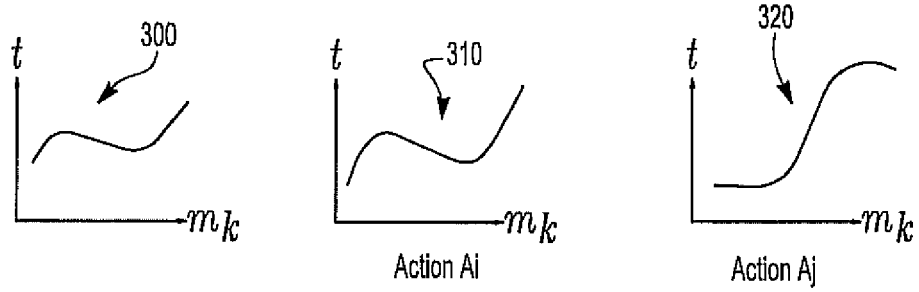
Fig-7
| 332 | 334 | 335 | 336 | 337 | 338 |
|---|---|---|---|---|---|
| Packet ID | Start time | Time elapsed | Magnitude | Candidate action No.s | Continue / End bit |
|  |  |  |  |  | 1.0 |
| Action | Active |
|---|---|
| Ax | 999 |
331 — 333
Fig-8

SYSTEM FOR RAPID DETECTION OF DROWSINESS IN A MACHINE OPERATOR

FIELD OF THE INVENTION

The present invention relates to a system for detecting drowsiness in a machine operator, and in particular, to a system having a facial action database with a plurality of stored high priority sleepiness facial actions that are used for rapidly detecting drowsiness in a machine operator.

BACKGROUND OF THE INVENTION

Accidents involving machines such as motor vehicles, heavy equipment machinery, metal stamping equipment and the like are known to occur when an operator of the machine becomes drowsy, distracted, etc. In an attempt to anticipate motor vehicle driver drowsiness, video monitoring systems that focus on the driver and capture images of the driver's facial characteristics are known. For example, U.S. Patent Application Publication No. 2007/0159344 discloses a system that processes three points of a driver's facial feature in order to calculate a head pose of the driver and determine their state during operation of a motor vehicle.

Other systems use facial imaging in order to determine behavior related to "road rage", "lying", drowsiness during monitoring of computer displays and the like. However, heretofore systems and methods have required excessive computation time and/or complex modeling of facial features in order to attempt an evaluation as to whether or not an individual is becoming or has become drowsy. As such, an improved system and/or process for rapidly detecting the drowsiness of an individual while operating a machine would be desirable.

SUMMARY OF THE INVENTION

The present invention discloses a system and a process for detecting drowsiness in an individual operating a machine. The system includes an image acquisition module that can electronically capture a plurality of facial images of the individual. In addition, the system has a face localization module with a generic face mesh grid (GFMG), the face localization module able to create a neutral face mesh grid (NFMG) by fitting the GFMG to a desired first captured facial image and a subsequent face mesh grid (SFMG) by fitting the GFMG to a desired second captured facial image.

A facial orientation module can also be included, the facial orientation module able to determine a variation between a facial orientation parameter of the neutral face mesh grid and an equivalent facial orientation parameter of the subsequent face mesh grid. Such a variation can be known as a facial variation. The facial action database having a plurality of stored high priority sleepiness facial actions can also be included with each of the stored high priority sleepiness facial actions having an assigned sleepiness severity value.

An action estimation module can compare the facial variation with the plurality of stored high priority sleepiness facial actions in the facial action database. In addition, one of the stored high priority sleepiness facial actions that matches the facial variation within a predetermined range of likeness can be selected. Thereafter, a matching module can identify and select any additional stored high priority sleepiness facial actions that are within a predetermined range of likeness to the initially selected stored high priority sleepiness facial action. A sleepiness level module can then compare the assigned sleepiness severity values of all the selected stored high priority sleepiness facial actions and generate a current level of sleepiness, the current level of sleepiness being the stored high priority sleepiness facial action corresponding to a sleepiness level that has the highest probability of being present in the individual. In addition, a warning module can actuate an actuator that can alert the individual as a function of the current level of sleepiness.

BRIEF DESCRIPTION OF THE DRAWINGS

FIG. 6 is a schematic illustration of a facial variation being submitted to and compared with a plurality of stored high priority sleepiness facial actions within a facial action database;

FIG. 7 is a schematic representation of the selection of additional stored high priority sleepiness facial actions that are within a predetermined range of likeness to a previously selected stored high priority sleepiness facial action;

FIG. 8 is a schematic representation of a trigger data packet;

DETAILED DESCRIPTION OF THE INVENTION

Figure 1:
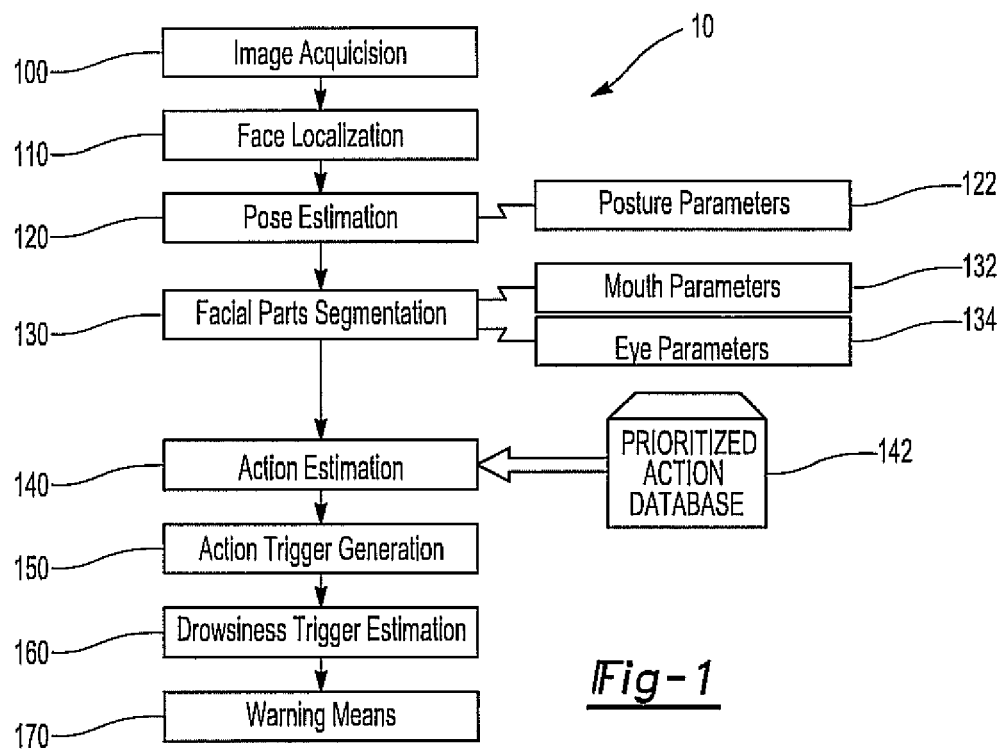
FIG. 1 is a schematic flowchart illustrating an embodiment of the present invention.

The present invention discloses a system for detecting drowsiness of an individual operating a machine. In addition, a process for detecting drowsiness in the individual is disclosed. As such, the present invention has utility as a safety feature for a machine.

The system can rapidly detect the drowsiness of an individual operating a machine and thereby improve the performance and/or safety of the individual, other individuals in the vicinity of the machine and the like. The system can include an image acquisition module that can electronically capture a plurality of facial images of the individual. In some instances, the individual can be a driver of a motor vehicle, an operator of heavy equipment machinery, an operator of metal stamping equipment and the like.

A face localization module can have a generic face mesh grid (GFMG) and be operable to create a neutral face mesh grid (NFMG) by fitting the GFMG to a desired first captured facial image. In the alternative, the GFMG can be a neutral model of a face and the NFMG determined by comparing the face mesh grids that have been fit to captured facial images until one of the fitted face mesh grids is selected because it is within a predetermined range of likeness of the GFMG. In yet another alternative, the NFMG can be determined by fitting the GFMG to a specific number of initial facial images and selected the face mesh grid that has the minimum difference with the GFMG. The eye and/or mouth regions of the NFMG can be segmented by tracing the boundaries of the eyes and/or mouths of the NFMG using a boundary tracing circuit. The boundaries of the eyes and/or mouth can be labeled and zero-motion parameters for the pose ($P_o$), eyes ($E_o$) and mouth ($M_o$) of the NFMG can be determined, stored as reference values and used in subsequent analyses.

The face localization module can create a subsequent face mesh grid (SFMG) by fitting the GFMG to a desired second captured facial image and a facial orientation module can be provided and used to determine a variation between a facial orientation parameter of the NFMG and an equivalent facial orientation parameter of the SFMG. Such a variation can be known as a facial variation. The facial variation can be a variation estimated from the zero-motion parameters of the NFMG and the pose, eyes and/or mouth parameters ($P=\{p_i\}$, $E=\{e_j\}$ and/or $M=\{m_k\}$) of the SFMG. It is appreciated that the pose parameter of the face mesh grids can be determined with respect to three-dimensional space.

Once the facial variation has been determined, an action estimation module can compare the facial variation to a plurality of high priority sleepiness facial actions (SHPSFAs) stored within a facial action database, also known as a prioritized action database. In some instances, each of the SHPSFAs can have an assigned sleepiness severity value that provides a degree of sleepiness to a given facial action. It is appreciated that some facial actions represent a greater degree of drowsiness than other facial actions. As such, the plurality of SHPSFAs with their assigned sleepiness severity values can provide a ranking of facial actions that are observed when the individual goes through various stages of drowsiness ranging from being fully awake to being fully asleep.

If the action estimation module identifies a SHPSFA that matches the facial variation within a predetermined range of likeness, a match trigger can be generated and the SHPSFA selected. In addition, a matching module can be used to identify and select any of the other SHPSFAs in the facial action database that are within a predetermined range of likeness to the initially selected SHPSFA. Thereafter, a sleepiness level module can evaluate all of the selected SHPSFAs with their assigned sleepiness values and estimate probabilities of current sleepiness levels. The sleepiness level module can also evaluate all of the selected SHPSFAs with prior probability estimates of current sleepiness levels and further estimate which SHPSFA has the highest probability and thus which sleepiness level has the highest probability of being present in the individual. Thereafter a drowsiness trigger can be generated for the current sleepiness level having the highest probability and a warning module can actuate an actuator that can alert the individual and/or other indivuals that may be in the near vicinity.

In some instances, the face localization module can have a facial landmark point circuit to select a set of facial landmark points on each of the plurality of captured images of the machine operator. It is appreciated that a facial landmark point can be a point on a facial image that can be easily and repeatedly identified by the face localization module. In addition, the face localization module can use the set of facial landmark points to fit the GFMD to the desired first captured facial image and any subsequent captured facial images.

Regarding the eye parameter and the mouth parameter, a facial parts segmentation module having a boundary tracing circuit can be provided. The boundary tracing circuit can trace an eye region and/or a mouth region of the SFMG and the NFMG with the eye parameter being a boundary of the eye region and the mouth parameter being a boundary of the mouth region. The facial parts segmentation module can calculate an eye region variation between the eye region boundaries of the SFMG and the NFMG ($E-E_o$) and a mouth region variation between the mouth region boundaries of the SFMG and the NFMG ($M-M_o$).

After a SHPSFA that matches the facial variation of the individual within a predetermined range of likeness has been selected, along with all SHPSFAs that are within a predetermined range of likeness to the initially selected SHPSFA, a trigger data packet module can generate a trigger data packet that contains data on all of the selected SHPSFA. Thereafter, a drowsiness trigger module can evaluate all of the selected SHPSA with their assigned sleepiness severity values and determine a probability for each candidate high priority sleepiness action. It is appreciated that the high priority sleepiness action with the highest probability can be associated with a level of drowsiness for the individual currently being experienced and can be known as the current level of sleepiness of current sleepiness level.

In some instances, the selected SHPSFAs with their assigned sleepiness severity values are compared with a previous current sleepiness level and used to estimate an updated or new current sleepiness level. In this manner, current facial variations can be compared and evaluated with previous facial actions and used to determine whether or not a particular captured facial image represents the individual becoming more drowsy or whether the captured image is simply a misleading indicator of drowsiness. After the current sleepiness level has been determined, an actuator can be actuated in order to alert the individual and/or surrounding individuals if required. In some instances, the actuator can be an audio actuator such as a beep, a radio in a motor vehicle, a bell, and the like. In other instances, a light actuator can be energized and/or a tactile actuator can be used to alert the individual that he or she is becoming drowsy and may fall asleep unless proper action is taken.

A process for rapidly detecting drowsiness in the individual can include capturing a plurality of facial images as a function of time an individual is operating a machine. For example and for illustrative purposes only, facial images of a driver for a motor vehicle can be taken at predetermined time intervals and may or may not be taken during short trips in the vehicle, for example short commuting trips to work, to run errands and the like. Stated differently, the system and the process has flexibility such that the manufacturer and/or the individual operating the machine can determine whether or not the system should be operated during short trips taken by a driver of a motor vehicle, small jobs performed by an operator of heavy equipment machinery and the like.

The process also includes selecting a set of facial landmark points on a desired first captured facial image and another set of facial landmark points on a desired second captured facial image. Thereafter, a NFMG can be created by fitting a GFMG to the set of facial landmark points on the desired first captured facial image and a SFMG can be created by fitting the GFMG to the set of facial landmark points on the desired second captured facial image. In the alternative, the GFMG can be a neutral model of a face and the NFMG created by comparing the face mesh grids that have been fit to captured facial images until one of the fitted face mesh grids is within a predetermined range of likeness of the GFMG and is thus selected. In yet another alternative, the NFMG can be created by fitting the GFMG to a specific number of initial facial images and the face mesh grid that has the minimum difference with the GFMG selected as the NFMG.

A facial variation can be calculated between pose, eye and/or mouth parameters of the NFMG and pose, eye, and/or mouth parameters of the SFMG. In addition, the facial variation can be compared with a plurality of SHPSFAs provided within a facial action database and one of the SHPSFAs selected if it is within a predetermined range of likeness to the facial variation.

The selected SHPSFA can then be compared with all of the plurality of SHPSFA in order to determine, and select, any candidate SHPSFAs that are similar to the initially selected SHPSFA within a predetermined range of likeness. Thereafter, a trigger packet is generated that contains data on all of the selected SHPSFAs and their assigned sleepiness severity values. A probability for each of the selected SHPSFA can be calculated and a current sleepiness level as a function of the SHPSFA having the highest probability can be determined. An actuator can then be actuated as a function of the current sleepiness level. In addition, previously calculated current sleepiness levels can be used and/or compared with the selected SHPSFAs and their assigned sleepiness severity values in order to estimate the current sleepiness level.

Turning now to FIG. 1, a schematic representation of an embodiment of the present invention is shown generally at reference numeral 10. The system 10 can have an image acquisition module 100 and a face localization module 110. A pose estimation module 120 can be included with posture parameters 122 and a facial parts segmentation module 130 can have mouth parameters 132 and eye parameters 134. The posture or pose parameters 122 can include head and body pose parameters. An action estimation module 140 can be in communication with a prioritized action database 142, also known as a facial action database. An action trigger generation module 150 and a drowsiness trigger generation module 160 can be included with the drowsiness trigger generation module 160 in communication with a warning module 170. It is appreciated that the various modules and/or circuits have been discussed above, the discussion of which will not be repeated here.

Figure 2:
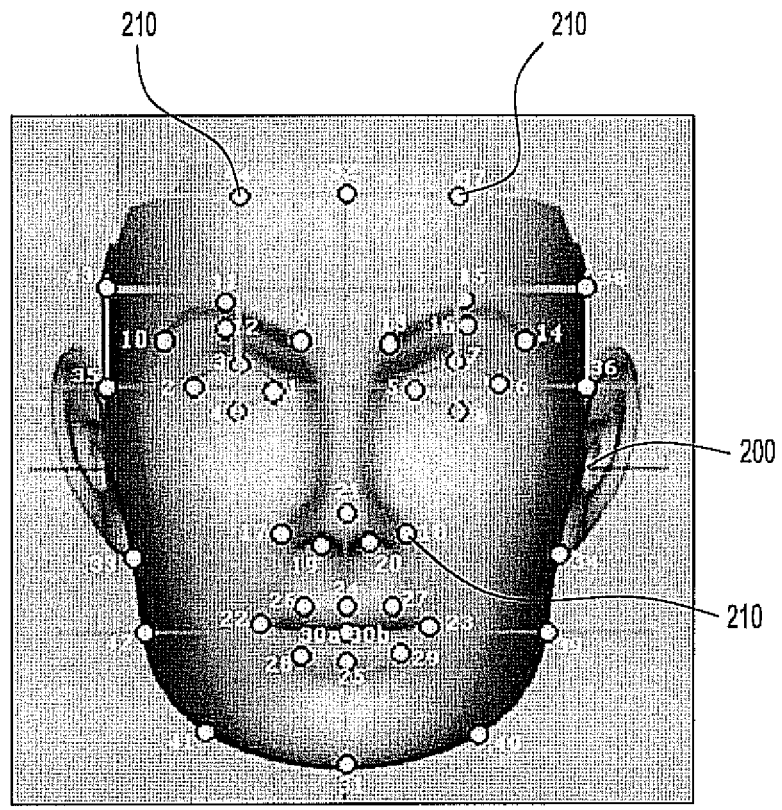
FIG. 2 is a schematic representation of a facial image representing facial landmark points thereon.

Referring now to FIG. 2, a schematic illustration of a facial image that has been captured by the image acquisition module 100 is shown. The facial image 200 can have a plurality of facial landmark points 210 that are generated by the face localization module 110. It is appreciated that the facial landmark points 210 can represent certain locations on the image 200 that are known to change as a function of drowsiness for an individual. As illustrated in FIG. 2, each of the facial landmark points can have a unique identifier such as a number, a letter, a combination thereof and the like.

Figure 3:
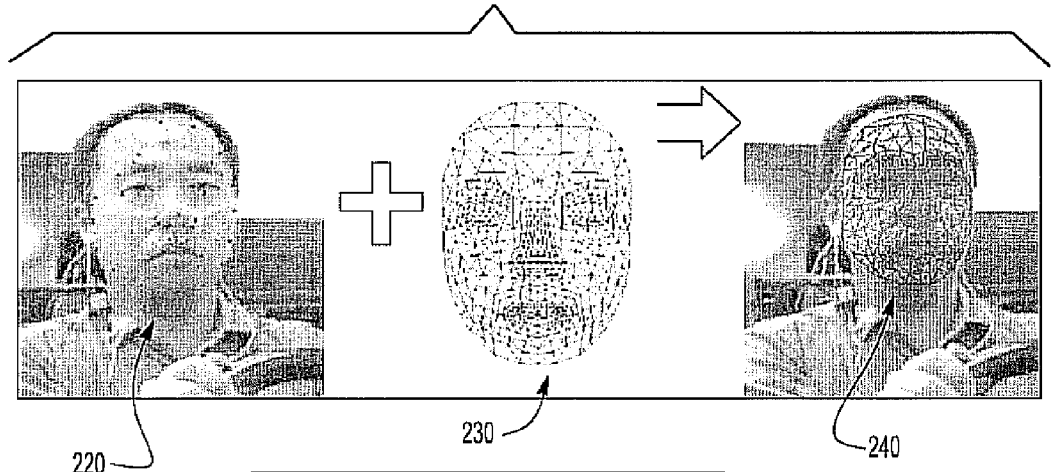
FIG. 3 is a schematic representation of a generic face mesh grid being fit to a facial image of an individual.

Referring to FIG. 3, a captured facial image 220 is shown with a plurality of facial landmark points 210 thereon. In addition, a GFMG 230 is fit to the facial landmark points 210 as illustrated at 240. In this manner, a GFMG can be fit to a captured image in order to create a NFMG and a SFMG. In addition, it is appreciated that the GFMG 230 can be fit to an image 220 that is an image of the individual showing signs of drowsiness such as yawning, nodding, partially closed eyelids and the like.

Figure 4:
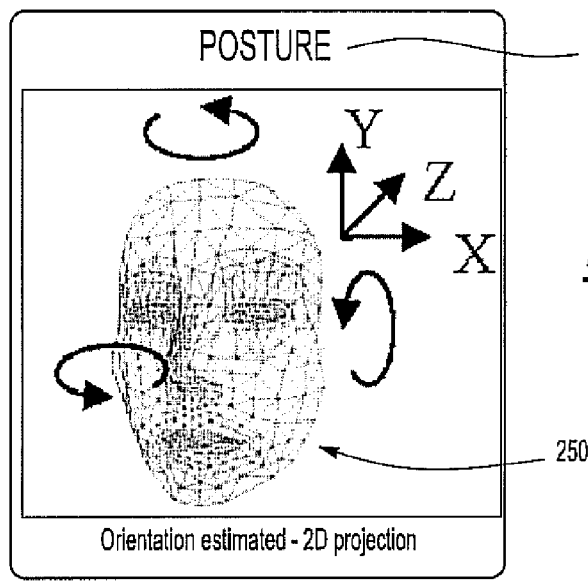
FIG. 4 is a schematic illustration of a pose parameter for a stored face mesh grid.

FIG. 4 illustrates the analysis of a face mesh grid 250 in order to determine the posture or pose 252 thereof. It is appreciated that the orientation is estimated from a two-dimensional projection and the pose or posture 252 is determined relative to three-dimensional space as symbolized by the X, Y and Z axes as shown in the figure. The posture 252 can be in the form of a pose parameter which may or may not be in the form of a vector.

Figure 5:
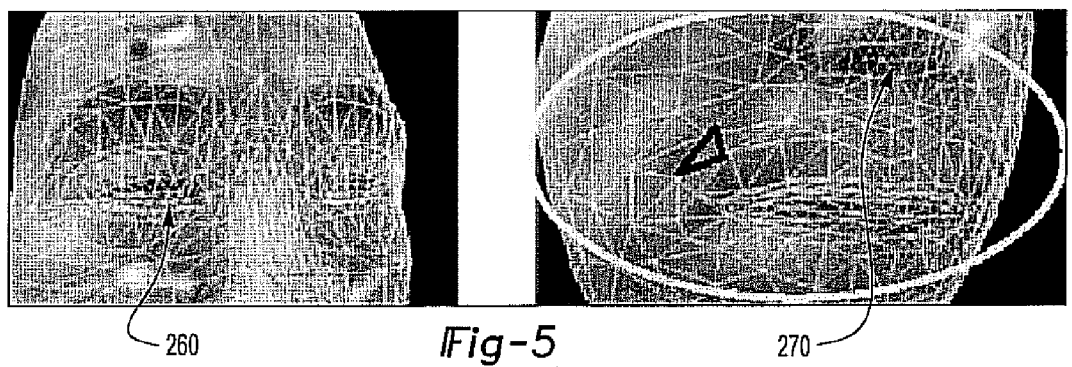
FIG. 5 is a schematic illustration of an eye boundary region and a mouth boundary region.

FIG. 5 illustrates the face mesh grid 230 in the areas of the eyes and the mouth after the grid 230 has been fit to a desired captured facial image. An eye region 260 and a mouth region 270 can have a plurality of grids that can be identified using a facial parts segmentation module. In addition, the facial parts segmentation module can have a boundary tracing circuit that can trace a boundary along the eye region 260 and the mouth region 270. In this manner, the eye region and the mouth region can be analyzed, with eye and mouth parameters generated, such that comparisons and variations between various images can be calculated and used for further analysis. For example, the zero-motion parameters can be determined and stored for further use. In addition, variations in the pose 252, the eye region 262 and the mouth region 272 can be used as input to a prioritized action database 280 that has a plurality of SHPSFAs as shown in phantom in FIG. 6 and illustratively labeled A1, A2, A3 . . . A17. The prioritized action database 280 with the plurality of SHPSFAs can represent or correspond to face mesh grids and/or facial images that represent various stages of drowsiness ranging from being completely awake to completely asleep.

Based on the comparison of the pose variation 252, eye variation 262 and/or mouth variation 272 with the stored SHPSFAs within the prioritized action database 280, one of the SHPSFAs can be selected if it is within a predetermined range of likeness to the pose variation 252, eye variation 262 and/or mouth variation 272. In some instances, an action estimation module with or without a comparison algorithm can be used to compare the pose variation 252, the eye variation 262 and/or the mouth variation 272 with the plurality of SHPSFA. Assuming a SHPSFA is selected, a matching module can select other SHPSFAs that are within a predetermined range of likeness to the initially selected SHPSFA. For example and for illustrative purposes only, FIG. 7 illustrates an initially selected SHPSFA 300, and two additional selected SHPSFAs 310 and 320 that are within a predetermined range of likeness of the SHPSFA 300.

Turning now to FIG. 8, an illustrative example of a trigger data packet 330 generated by an action trigger generation module is shown. The trigger data packet 330 is a function of all the selected SHPSFAs, e.g. SHPSFAs 300, 310 and 320. As shown in this figure, the trigger data packet 330 can have a packet ID 332, a start time 334, a time elapsed 335, a magnitude 336, a candidate action number or numbers 337 and a continue or end function 338. It is appreciated that each of the items in the data packet 330 can be further itemized as shown by the packet ID 332 being split into an action 331 and an active 333 category. A drowsiness trigger module can evaluate the data within the data packet 330 and determine a candidate sleepiness action with a highest probability to be present for the individual.

Regarding determining which SHPSFA is determined to have the highest probability of being exhibited by the individual, an action prioritizing circuit can learn and/or be programmed such certain SHPSFAs are known to be present more likely during different stages of sleepiness than other stages. In addition, the facial action database can have global values, i.e. facial variations that can be extracted from a test population, and once an individual is recognized to the system for the first time, i.e. a NFMG is created for the individual, the facial action database can be used for initial priority rating of the facial variation(s) submitted thereto. In addition, the priority rating can be based on single action or action combinations for the individual that occur at different levels of sleepiness.

Figure 9:
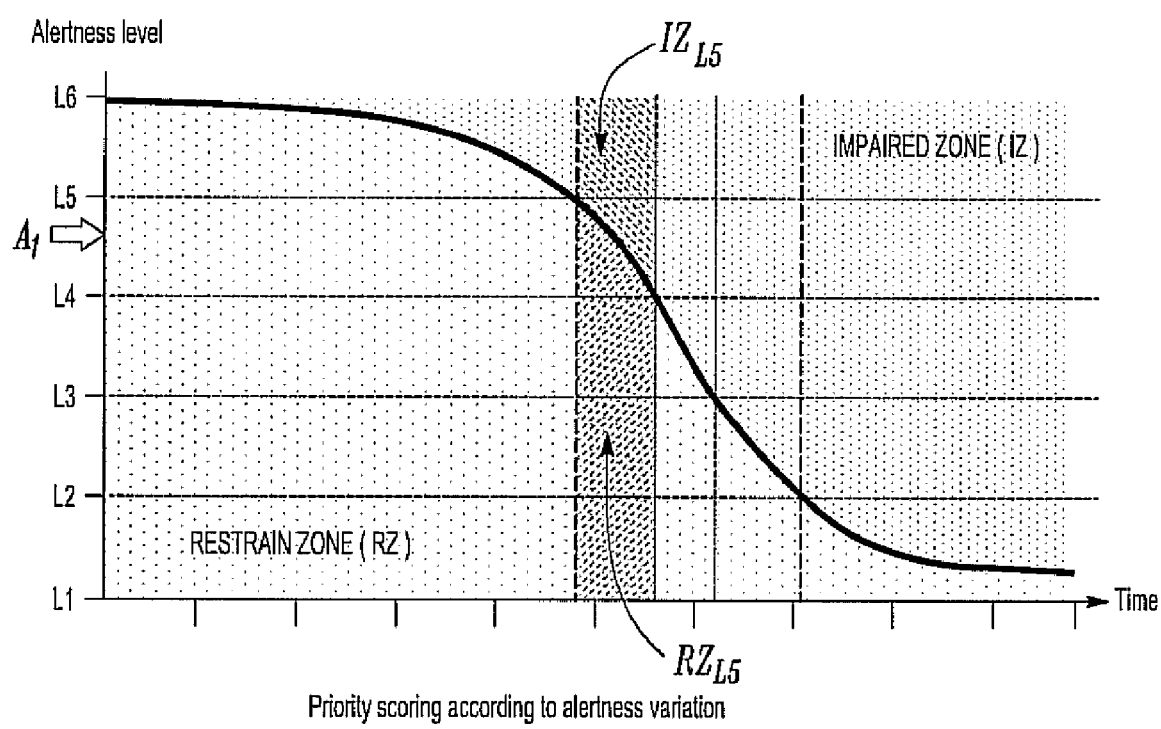
FIG. 9 is a graphical representation of alertness level as a function of time.

For example, FIG. 9 illustrates how a priority rating for a given action $A_i$ can be determined. A graph has an X-axis for time and a Y-axis for alertness level. Assuming $IZ_{L5}$ represents an impaired zone of drowsiness and $RZ_{L5}$ represents a restrain zone, and further assuming that the action $A_i$ occurs predominately at level L5 rather than at other alertness levels, a priority score for the action $A_i$ as shown in the graph can be determined by the ratios of $IZ_{L5}$ and $RZ_{L5}$. One such ratio can be expressed as:

$$\xi = \frac{IZ_{L5}}{RZ_{L5}} \cdot \alpha$$

where α is an alertness level specific scalar related to the location of the level the action occurred. As such ξ discriminates actions occurring within different regions of a given alertness level. It is appreciated that actions occurring at different alertness levels are assigned different priority values.

Figure 10:
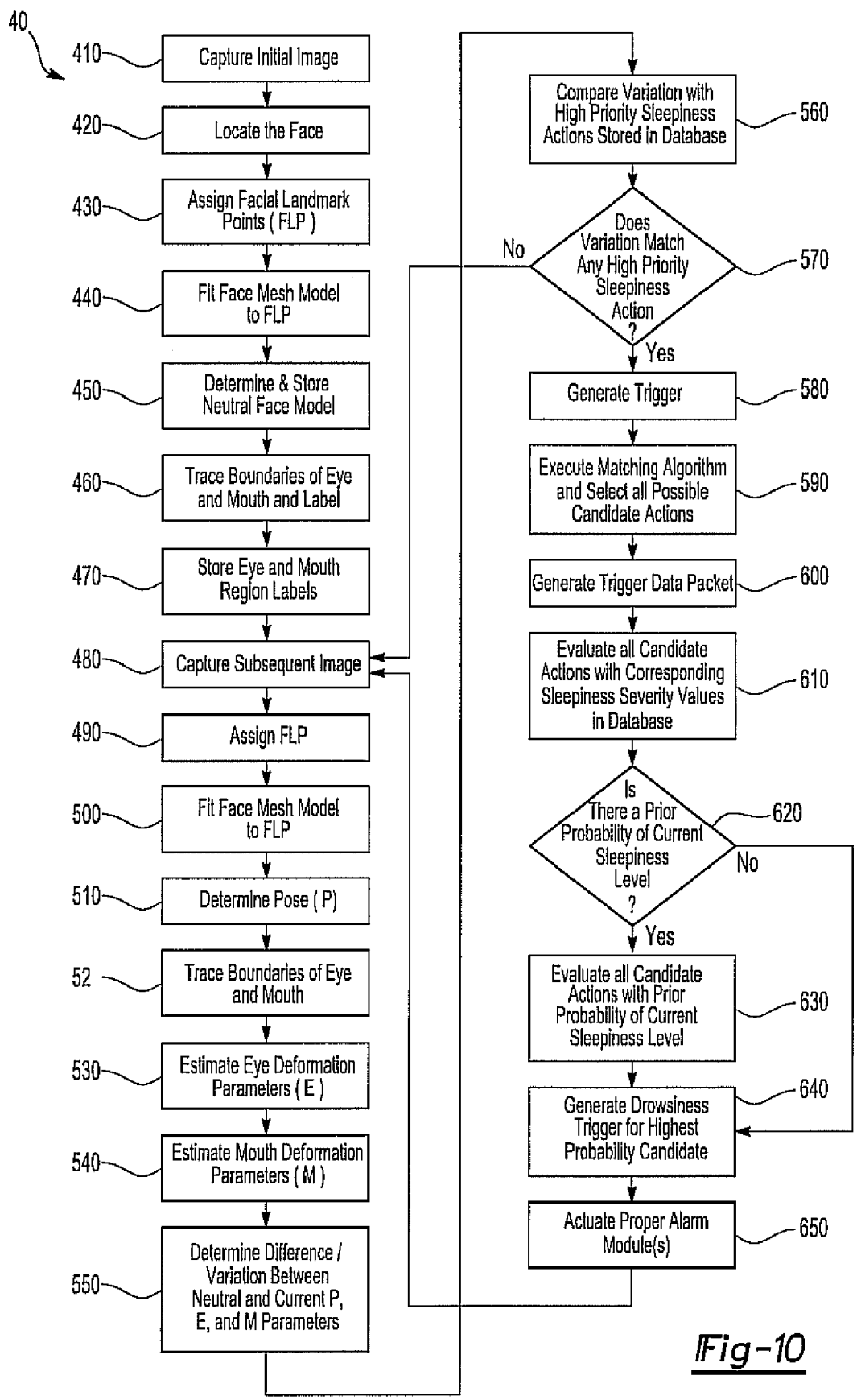
FIG. 10 is a flowchart illustrating a process for an embodiment of the present invention.

Turning now to FIG. 10, a flowchart illustrating a process for rapidly detecting drowsiness in an individual operating a machine is shown generally at reference numeral 40. The process 40 can include capturing an initial image at step 410 followed by locating the face in the captured image at step 420. Thereafter, facial landmark points can be assigned to the face in the captured image at step 430 and a face mesh model, a GFMG, etc., can be provided and fit to the facial landmark points at step 440. Using the face mesh model that has been fit to the facial landmark points, a NFMG, also known as a neutral face model, can be determined and stored at step 450. Thereafter, the boundaries of the eyes and the mouth can be traced and labeled at step 460 and stored at step 470.

A subsequent image can be captured at step 480. Similar to the capturing of the initial image at step 410, a face in the subsequent captured image can be located and assigned facial landmark points at step 490. Thereafter, a face mesh model can be fit to this subsequent captured image in order to create a SFMG using the facial landmark points at step 500. The pose of the captured subsequent image can be determined at step 510 and the boundaries of the eye and the mouth can be traced at step 520. The variation between the pose, eye and mouth regions can be calculated with eye deformation parameters estimated at step 530 and mouth deformation parameters estimated at step 540. It is appreciated that the eye deformation parameters and the mouth deformation parameters can be in the form of a vector, a scaler and the like.

At step 550, the difference and/or variation between neutral and subsequent facial image pose, eye and mouth parameters can be determined, followed by comparison of the variation in these parameters with SHPSFAs in a prioritized database at step 560. Whether or not the variation in the parameters matches any of the SHPSFAs within a predetermined range of likeness can be determined at step 570. If there is not a match, the process can return to step 480 where another subsequent image is captured and the process continues from there. In this manner, the system and the process can continually capture images of the individual and evaluate whether the initiation of drowsiness is occurring, or if has already occurred, to what extent it has progressed.

In the alternative, if a variation is matched with one of the SHPSFAs, the SHPSFA can be selected and a trigger related to the selected SHPSFA can be generated at step 580. Thereafter a matching algorithm can be used to select all possible candidate SHPSFAs that are within a predetermined range of likeness to the initially selected SHPSFA at step 590. Upon selecting all possible candidate SHPSFAs at step 590, a trigger data packet is generated at step 600 and all of the candidate actions with corresponding sleepiness severity values in the database are evaluated at step 610.

At step 620, whether or not a prior probability of a current sleepiness level has been determined is evaluated. If a prior probability of current sleepiness level has not been previously determined, the process can skip to step 640 wherein a drowsiness trigger for a highest probability candidate SHPSFA is generated, i.e. the SHPSFA that corresponds to a current sleepiness level of the individual that is most likely to be present is determined. In the alternative, if a prior probability of current sleepiness level has been determined, the process can proceed to step 630 where all candidate actions with their assigned sleepiness severity values can be evaluated with prior probability of current sleepiness levels to generate a drowsiness trigger for a highest probability candidate action at step 640. After step 640, a proper alarm module or modules can be actuated at step 650. Thereafter, the process can return to step 480 in which subsequent images can be captured.

In this manner, a process is provided for rapidly detecting drowsiness in a machine operator. In particular, pose deformation parameters, eye deformation parameters and mouth deformation parameters can be used for comparison with facial sleepiness actions stored in a prioritized database. For example, if the pose deformation parameters, eye deformation parameters and/or mouth deformation parameters identify a yawn within the high priority sleepiness actions stored in the prioritized database, such a facial action can be used to compare with previous facial actions and generate an appropriate alarm for the driver and/or individuals within a motor vehicle, an operator of heavy equipment machinery and the like.

The foregoing drawings, discussion and description are illustrative of specific embodiments of the present invention, but they are not meant to be limitations upon the practice thereof. Numerous modifications and variations of the invention will be readily apparent to those of skill in the art in view of the teaching presented herein. It is the following claims, including all equivalents, which define the scope of the invention.

I claim:

1. A system for detecting drowsiness in a machine operator, the system comprising:

an image acquisition module operable to electronically capture a plurality of facial images of the machine operator;

a face localization module having a generic face mesh grid, said face localization module operable to create a neutral face mesh grid by fitting said generic face mesh grid to a desired first captured facial image, said face localization module also operable to create a subsequent face mesh grid by fitting said generic face mesh grid to a desired second captured facial image;

a facial orientation module operable to determine a facial variation between a facial orientation parameter of said neutral face mesh grid and a facial orientation parameter of said subsequent face mesh grid;

a facial action database having a plurality of stored high priority sleepiness facial actions, said plurality of stored high priority sleepiness facial actions each having an assigned sleepiness severity value;

an action estimation module having a comparison algorithm, said action estimation module operable to compare said facial variation with said plurality of stored high priority sleepiness facial actions using said comparison algorithm and select a stored high priority sleepiness facial action that matches said facial variation within a predetermined amount;

a matching module operable to identify and select stored high priority sleepiness facial actions that are within a predetermined range of likeness to said identified stored high priority sleepiness facial action;

a sleepiness level module operable to compare assigned sleepiness values of all selected stored high priority sleepiness facial actions and generate a probability of a current level of sleepiness;

a warning module operable to actuate an actuator as a function of the current level of sleepiness having a highest probability.

2. The system of claim 1, wherein said face localization module has a facial landmark point circuit operable to select a set of facial landmark points on each of said plurality of captured images.

3. The system of claim 2, wherein said face localization module uses said set of facial landmark points to fit said generic face mesh grid to said desired first captured facial image and said desired second captured facial image.

4. The system of claim 1, wherein said facial orientation parameter is selected from the group consisting of a pose parameter, an eye parameter, a mouth parameter and combinations thereof.

5. The system of claim 4, wherein said facial orientation module has a circuit selected from the group consisting of a pose estimation circuit, a facial parts segmentation circuit and combinations thereof.

6. The system of claim 5, wherein said pose estimation circuit is operable to calculate a pose variation between a pose parameter of said subsequent face mesh grid of the operator in three-dimensional space and a pose parameter of said neutral face mesh grid in three-dimensional space of the operator.

7. The system of claim 5, wherein said facial parts segmentation circuit has a boundary tracing circuit selected from the group consisting of an eye region tracing circuit, a mouth region tracing circuit and combinations thereof, said eye region tracing circuit operable to trace an eye region on a face mesh grid and create said eye parameter and said mouth region tracing circuit operable to trace a mouth region on said face mesh grid and can create said mouth parameter.

8. The system of claim 7, wherein said eye parameter is an eye region boundary and said mouth parameter is a mouth region boundary.

9. The system of claim 8, wherein said facial parts segmentation circuit is operable to calculate an eye region variation between an eye region boundary of said subsequent face mesh grid and an eye region boundary of said neutral face mesh grid of the operator.

10. The system of claim 9, wherein said facial parts segmentation circuit is operable to calculate a mouth region variation between a mouth region boundary of said subsequent face mesh grid and a mouth region boundary of said neutral face mesh grid of the machine operator.

11. The system of claim 1, further comprising a trigger data packet module operable to generate a trigger data packet containing data on all selected stored high priority sleepiness facial actions.

12. The system of claim 11, further comprising a drowsiness trigger module operable to evaluate said selected stored high priority sleepiness facial actions with said assigned sleepiness values with a previous probability of current sleepiness level and determine a highest probability candidate high priority sleepiness action.

13. The system of claim 12, wherein said drowsiness trigger module generates a drowsiness trigger as a function of said highest probability candidate high priority sleepiness action.

14. The system of claim 1, wherein said actuator is selected from the group consisting of an audio actuator, a light actuator, a tactile actuator and combinations thereof.

15. A process for detecting drowsiness in a machine operator, the process comprising:
capturing a plurality of facial images as a function of time the operator is operating the machine;
selecting a set of facial landmark points on a desired first captured image;
selecting a set of facial landmark points on a desired second captured image;
creating a neutral face mesh grid by fitting a generic face mesh grid to the set of facial landmark points on the desired first captured facial image;
creating a subsequent face mesh grid by fitting the generic face mesh grid the set of facial landmark points on the desired second captured facial image;
calculating a facial variation between the neutral face mesh grid and the subsequent facial mesh grid;
providing a facial action database having a plurality of stored high priority sleepiness facial actions, said plurality of stored high priority sleepiness facial actions each having an assigned sleepiness severity value;
comparing the facial variation to the plurality of stored high priority sleepiness facial actions;
selecting one of the stored high priority sleepiness facial actions that is within a predetermined range of likeness of the facial variation;
comparing the selected stored high priority sleepiness facial action with all of the plurality of stored high priority sleepiness facial actions;
selecting all of the stored high priority sleepiness facial actions that are similar to the selected one stored high priority sleepiness facial action within a predetermined range of likeness;
generating a trigger packet containing data on all of the selected stored high priority sleepiness facial actions;
evaluating all of the assigned sleepiness severity values for all of the selected stored high priority sleepiness facial actions;
calculating a probability for each of the selected stored high priority sleepiness facial actions;
calculating a current sleepiness level as a function of the selected stored high priority sleepiness facial action having a highest probability; and
actuating an actuator as a function of the current sleepiness level.

16. The process of claim 15, further including:
evaluating the current sleepiness level with a previous selected stored high priority sleepiness facial action having the highest probability;
calculating an updated current sleepiness level as a function of the evaluation of the current sleepiness level with the previous selected stored high priority sleepiness facial action having the highest probability.

* * * * *